US010173317B2

(12) United States Patent
Sato et al.

(10) Patent No.: US 10,173,317 B2
(45) Date of Patent: Jan. 8, 2019

(54) MULTI-ARTICULATED MANIPULATOR

(71) Applicant: NIPPON THOMPSON CO., LTD., Tokyo (JP)

(72) Inventors: Takashi Sato, Mino (JP); Tetsuya Sakai, Mino (JP)

(73) Assignee: NIPPON THOMPSON CO., LTD., Tokyo (JP)

( * ) Notice: Subject to any disclaimer, the term of this patent is extended or adjusted under 35 U.S.C. 154(b) by 394 days.

(21) Appl. No.: 15/045,399

(22) Filed: Feb. 17, 2016

(65) Prior Publication Data

US 2016/0243697 A1 Aug. 25, 2016

(30) Foreign Application Priority Data

Feb. 25, 2015 (JP) ................................. 2015-034905

(51) Int. Cl.
| | |
|---|---|
| *B25J 9/10* | (2006.01) |
| *B25J 17/02* | (2006.01) |
| *B25J 15/00* | (2006.01) |
| *A61B 1/008* | (2006.01) |
| *A61B 34/00* | (2016.01) |

(Continued)

(52) U.S. Cl.
CPC ................ *B25J 9/10* (2013.01); *A61B 34/70* (2016.02); *B25J 9/06* (2013.01); *B25J 15/0028* (2013.01); *B25J 15/022* (2013.01); *B25J 17/025* (2013.01); *A61B 1/008* (2013.01); *A61B 2017/2908* (2013.01); *A61B 2017/2927* (2013.01); *Y10S 901/19* (2013.01); *Y10S 901/25* (2013.01); *Y10S 901/27* (2013.01); *Y10S 901/36* (2013.01)

(58) Field of Classification Search
CPC ....... B25J 9/10; B25J 9/106; B25J 9/06; B25J 9/065; B25J 15/022; B25J 15/0028; B25J 17/025; A61B 1/008; A61B 34/70; A61B 2017/2908; A61B 2017/2927; A61B 2017/2932; Y10S 901/36
See application file for complete search history.

(56) References Cited

U.S. PATENT DOCUMENTS 3,610,058 A * 10/1971 Mueller ..................... B25J 9/06
                                                                137/355.16
5,817,119 A * 10/1998 Kliennan ............... A61B 17/29
                                                                606/174

(Continued)

FOREIGN PATENT DOCUMENTS

| JP | 2005169011 A | 6/2005 |
| JP | 2007292276 A | 11/2007 |

(Continued)

*Primary Examiner* — Jake Cook
*Assistant Examiner* — Bobby Rushing, Jr.
(74) *Attorney, Agent, or Firm* — Browdy and Neimark, PLLC

(57) ABSTRACT

A multi-articulated manipulator composed of more than one hollow outer shell, joints to connect the outer shells to each other, a grasping member fastened for rotating movement with respect to the proximal outer shell, a claw transmission shaft to actuate the grasping member to rotate and an outer shell power transmission shaft to actuate the outer shells in to rotate independently from each other. The claw transmission shaft and the outer shell power transmission shaft respectively are composed of universal joints capable of rotating force and transmitting torque.

12 Claims, 8 Drawing Sheets

(51) Int. Cl.
B25J 9/06 (2006.01)
B25J 15/02 (2006.01)
*A61B 17/29* (2006.01)

(56) References Cited

U.S. PATENT DOCUMENTS 8,257,387 B2 * 9/2012 Cunningham ......... A61B 17/29
 606/206
9,956,043 B2 * 5/2018 Farritor ............ A61B 17/00234
2014/0379014 A1 * 12/2014 Abri .................. A61B 17/2804
 606/170

FOREIGN PATENT DOCUMENTS

JP 2011083476 A 4/2011
JP 2013252338 A 12/2013

* cited by examiner

MULTI-ARTICULATED MANIPULATOR

FIELD OF THE INVENTION

The present invention relates to a manipulator or a forceps having more than one articulation, which is adapted for a variety of instruments applied to for example medical robots, medical instruments, manipulators and the like.

BACKGROUND OF THE INVENTION

A driving mechanism for surgical use is disclosed in, for example, Published Unexamined Patent Application in Japan No. 2007-292 276, which is energized with an input of rotation to enable bending (rotating) and/or curving of a connection part. With the driving mechanism as cited earlier, the manipulator has a bending link to join connecting members together and grasping links. The grasping links are connected to the connecting members in such a way as to prohibit movement in the axial direction. The grasping links each have a first shaft and a second shaft, the first shaft having second male threads mating with a second plate of the connecting member and the second shaft having first male threads mating with a first plate of the connecting member. The first and second male threads are made inversely with respect to each other with the same pitch. With the relation of the male threads around the shafts, the connecting members move to approach each other when the bending link is rotated in one direction, whereas the connecting members move away from each other when the bending link is rotated in the opposite direction.

Moreover, a multi-degree-of-freedom manipulator is disclosed in, for example, Published Unexamined Patent Application in Japan No. 2005-169 011, which has superior durability and control accuracy, and further is easier to attach to and/or detach from the sterilizers, washers and driving means. The multi-freedom manipulator has at least three degrees of freedom of relative opening/closing movement of a pair of grasping members, rotation of grasping members around a first axis, and rotation of the grasping members around a second axis lying on an imaginary plane perpendicular to the first axis. With the multi-degree-of-freedom manipulator constructed as stated earlier, the power applied from the actuator is converted through one to three link mechanisms into relative opening/closing movement of the grasping members, rotating movement around a first axis and rotating movement around a second axis.

With the medical manipulator, moreover, the working parts on the proximal ends of the forceps are actuated with wires for power transmission. In Published Unexamined Patent Application in Japan No. 2011-83 476, there is disclosed a medical manipulator in which the forceps is operated without urging the wire against one of the arms of the forceps. The medical forceps usually has a pair of operable arms, operating means allowing any one of first pulling wire and second pulling wire to pull towards a base end while another pulling wire is pulled towards a proximal end, and a power transmission mechanism among the arms and the operating means. With the power transmission mechanism constructed as stated earlier, a pair of pulling wires and a pair of second wires are connected each other through a pair of opening/closing members. Thus, just as the first pulling wire is pulled towards the base end thereof, the second pulling wire is pulled towards the proximal end thereof and the opening/closing members are moved towards closing phase. Moreover, just as the second pulling wire is pulled towards the base end thereof, the first pulling wire is pulled towards the proximal end thereof and the opening/closing members are moved towards opening phase.

Disclosed in, for example, Published Unexamined Patent Application in Japan No. 2013-252 338, there is disclosed a medical treatment member which has a first bendable tubular member lying on a proximal end side, a first wire member whose one end is fixed to the proximal end of the first bendable tubular member and another end disposed for rotation on a proximal end of the first bendable tubular member and a driving mechanism provided to rotate another end of the first wire member. The first wire member causes a twisted condition owing to the rotation of another end of the first wire member, thereby generating the stress in the shrinkage direction between the opposite ends of the first wire member to get the first tubular member bending.

Subject to be Solved with the Present Invention

With the prior wire-operated medical forceps constructed as stated earlier, the working ends on the forceps are mainly actuated through the power transmission of wires. Thus, there have been problems to be solved in the follow-up and response involved with time lag caused by variation in tension of the wire which is subject to expansion and contraction. With the prior wire-operated medical forceps, there are problems in which the wire has been ruptured or cut, or elongation and tensile variation in wire elongation and shrinkage causes a loss of accurate operation and which worsens follow-up and response in operation of the certain power transmission. With the conventional power transmission constructed as stated earlier, the rotation of the connecting part is transferred to the connecting part to cause it to bend or curve. However, the driving part as a whole is driven to bend by the combination of a limiting universal joint with a driving universal joint. With the power transmission made in small-sized construction, thus, there is a problem in which the housing constructed with three universal joints may have a larger flexibility or warp but will be less rigid. This means that the joints are not allowed to bend independently from each other, therefore fine movements become difficult. With the multi-degree-of-freedom manipulator constructed as stated earlier, the linkage part is actuated with fore and aft movement transmitted from the actuator to move the joints in biaxial vertical and horizontal directions. Nevertheless, the manipulator constructed as stated earlier is unsuited for fine movement for every joint and involves a problem of have a slender and longer linkage part which is apt to be less rigid.

Disclosed in co-application No. 2015-9 257 in Japan is the medical forceps which is rich in reliability and follow-up property and further can be operated with high accuracy. The prior forceps of multi-articulated construction is composed of more than one hollow outer sleeves, joint members fastened to opposite ends of each of the hollow outer sleeves to pivotally connect together the opposite ends of each hollow outer sleeve to join together the adjacent hollow sleeves, a grasping member fastened in a pivotal manner to the proximal sleeve to hold or grasp any object, and a power transmission shaft to actuate the grasping member and the hollow outer sleeves to bend independently from each other. The power transmission shaft has more than one universal joint capable of moving to transmit any torque and a transmission shaft which is extensible and capable of transmitting the torque. With the multi-articulated forceps constructed as stated earlier, as multiple opposing sleeves are allowed to operate independently from each other, it is required to increase the number of power transmission shafts fit in the outer sleeves. This results in a large diameter of the outer sleeve as well as restricted bending angles of every outer sleeve.

SUMMARY OF THE INVENTION

The present invention has for its primary object to resolve the major problems as stated earlier, and to provide a manipulator of multi-articulated construction particularly suitable for medical instruments, which comprises a plurality of hollow outer shells lying lengthwise in series, grasping members mounted on the proximal outer shell to grasp other objects, joint members to connect the opposed outer shells, and a power transmission shaft to actuate the outer shells to bend with respect to one another. The grasping members have a pair of claw members which are allowed to make opening/closing movement independently from each other and/or bending movement in same direction by means of a pair of claw power transmission shafts. Moreover, both the outer shell and the power transmission shaft are made of metallic material to ensure sufficient rigidity, thereby being staved off from any tensile variation due to expansion/shrinkage which results from material of the power transmission shaft. Thus, the power transmission shaft to be fit in the outer shell may be reduced in number and therefore the outer shell is allowed to reduce in diameter. As a result, the actuation of the outer shell and claw members caused by the operation of the power transmission shaft is improved in its response and follow-up properties, thereby making it possible to accurately move the claw members lying on the proximal outer shell towards a predetermined attitude.

Means to Solve the Problems

The present invention relates to a multi-articulated manipulator having a driving means which comprises a plurality of hollow outer shells arranged in series in a lengthwise direction, an articulation that connects adjoining joints of the outer shells to bend, grasping members connected to bend with respect to a proximal one of the outer shells, a power transmission shaft fit to the outer shells to operate the grasping members for extending, contracting and bending the grasping members, and a linkage mechanism connecting the power transmission shaft with the outer shell at the articulation to rotate the outer shells, synchronizing the rotating movement in the same direction of the proximal outer shell and the intermediate outer shell, wherein the power transmission shaft is composed of a proximal outer shell constituting one of the outer shells and operating a pair of claw members for the grasping members independently from each other, a pair of claw power transmission shafts fit in an intermediate outer shell and a distal outer shell and mounted for rocking movement, and outer shell power transmission shafts fit in the distal outer shell and intermediate outer shell to be able to bend the proximal outer shell and the intermediate outer shell in the same direction and further fastened in a rocking manner to the distal outer shell and the intermediate outer shell, wherein the linkage mechanism has a nut having female threads mating with male threads formed on the claw power transmission haft and the outer shell power transmission shaft, and a linkage member connecting the nut with the outer shell, and wherein upon rotation of the claw power transmission shaft, the nut moves axially along the male threads and the linkage mechanism moves in association with the movement of the nut so as to make opening/closing movement or bending movement in the same direction of the claw members of the grasping members, and further upon rotation of the outer shell power transmission shaft, the nut moves axially along the male threads and at the same time linkage mechanism is operated to bend the adjacent outer shells relatively to each other.

The driving means has more than one transmission shaft constructed to extend and shrink under the action of springs, a universal joint to connect to rotate the transmission shafts, and more than one linking member to constitute the linkage mechanism to connect the outer shells to bend with respect to one another.

Moreover, the transmission shaft is made in extending manner of the spring, a shaft portion fit with the spring and a cylinder member fit so as to extend over the shaft portion under the resilient force of the spring.

The articulation makes it possible to bend the grasping members relatively to each other, the proximal outer shell and the intermediate outer shell around respective fulcrum pins extending through connecting portions between the grasping members and the outer shell to fasten in a bending manner between the grasping members and the proximal outer shells and between the proximal outer shell and the intermediate outer shell, and between the intermediate outer shell and the distal outer shell. Moreover, the linkage member of the linkage mechanism is connected so as to rock or rotate at one end thereof with respect to the nut and at another end thereof with respect to the outer shell and further connected so as to rock or rotate at the biased location to the fulcrum pin.

The joint is composed of a proximal articulation to make a pair of the claw members of the grasping members close and open or bend in the same direction, an intermediate articulation to bend the proximal outer shell relatively to the intermediate outer shell, and a distal articulation to bend the intermediate outer shell with respect to the distal outer shell. Moreover, a pair of claw members for the grasping members is supported to rock or rotate around the fulcrum pin to the connection fastened to an end of the proximal outer shell to make opening and closing movement or unidirectional bending movement.

The claw power transmission shaft is composed of a proximal power transmission shaft fit in the proximal outer shell, an intermediate power transmission shaft arranged inside the intermediate outer shell and coupled for rotation to the proximal power transmission shaft through a first universal joint, and a distal power transmission shaft installed in the distal outer shell and coupled for rotation to the intermediate power transmission shaft through a second universal joint. Moreover, the outer shell power transmission shaft is composed of an intermediate power transmission shaft arranged in the intermediate outer shell, and a distal power transmission shaft installed in the distal outer shell and connected for rotation to the intermediate power transmission shaft through a third universal joint.

The proximal articulation lying between the proximal outer shell and the grasping members has the linkage member fastened to rotate at a driving action point biased from a rotating center of a boss portion of the claw member having the fulcrum pin as the center of rotation, whereby the nut, linkage member and boss portion work together to open and close the claw members or bend them in the same direction.

The intermediate articulation lying between the proximal outer shell and the intermediate shell has a linkage member which is installed to rotate around a fulcrum point in the nut mated with the outer shell power transmission shaft in the intermediate outer shell and at a driving action point in the proximal outer shell biased from a center of rotation of the fulcrum pin of the proximal outer shell, and wherein the proximal outer shell the nut, linkage member and the proximal outer shell lying in the intermediate outer shell work together to make the proximal outer shell bend with respect to the intermediate outer shell, thereby bending the proximal outer shell relatively to the intermediate outer shell. Moreover, the distal articulation between the intermediate outer shell and the distal outer shell is composed of a first linkage member supported in a rocking or rotating manner to a first point of driving action biased from a center of rotation of the fulcrum pin point on the distal outer shell and a fulcrum point on the nut mated with the outer shell power transmission shaft lying along the distal outer shell, a second linkage member supported in a rocking or rotating manner around another fulcrum pin to a second point of driving action and a third point of driving action biased from a center of rotation of the fulcrum point on the distal outer shell, and a third linkage member fastened for rocking or rotating movement to the second point of driving action and a third point of driving action lying on the intermediate outer shell biased from a center of rotation of the fulcrum pin, whereby rotating movement of the outer shell power transmission shaft drives the nut lying on the distal outer shell, the first and second linkage members and the third linkage member, so that the intermediate outer shell and the proximal outer shell are allowed to work together to cause the bending movement.

The outer shell and the power transmission shaft are made of metallic material to have a previously determined rigidity.

Effect of the Invention

The multi-articulated manipulator of the present invention as described above is constituted with the distal outer shell arranged in the axial direction, three outer shells of the intermediate outer shell and the proximal outer shell, the grasping members connected to the proximal outer shell, and the driving means of three power transmission shafts fit in the outer shells. The driving means is composed of the power transmission shaft constituted with a pair of the claw power transmission shaft and the outer shell power transmission shaft, the nut fastened to the power transmission shaft, and the linkage mechanism connecting the nut and the outer shell. Thus, there is no expansion and contraction arising from the material of the power transmission and, therefore, the claw members on a pair of claw power transmission shafts may realize fine movement independently from each other. Only one outer shell power transmission shaft gets the intermediate outer shell working together with the proximal outer shell in a bending operation across wide bending angles, so that the claw power transmission shaft makes it possible to quickly actuate the grasping members independently from each other to make opening and closing movements or bending movement rich in follow-up properties in the same directions, thereby moving the grasping members to a predetermined position while keeping the desired attitude. Moreover, as the male threads around the power transmission shaft mate with the nut on the boss portion of the outer shell, only rotating the power transmission shaft pushes and pulls the linking members of the linkage mechanism to immediately rotate the intermediate shell and the proximal outer shell across a wide angular range. In addition, the multi-articulated manipulator of the present invention is rich in reliability in operation and better in follow-up properties to move the grasping members to the preselected bending location accurately. Especially, the multi-articulated manipulator of the present invention is better for realizing the desired movement of the medical forceps.

DETAILED DESCRIPTION OF THE EMBODIMENT

Figure 1:
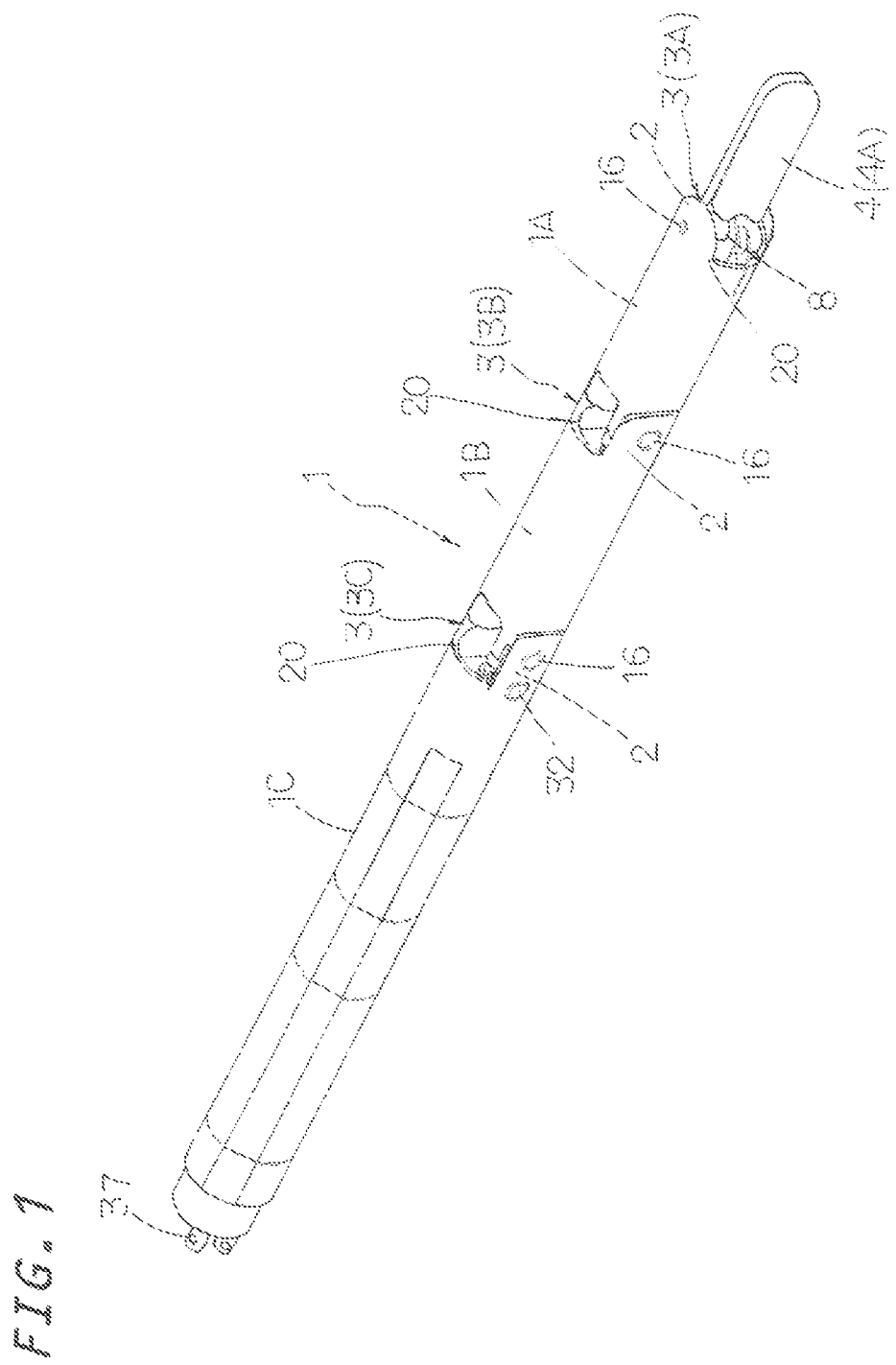
FIG. 1 is a perspective view showing a preferred embodiment of a multi-articulated forceps according to the present invention.
Figure 2:
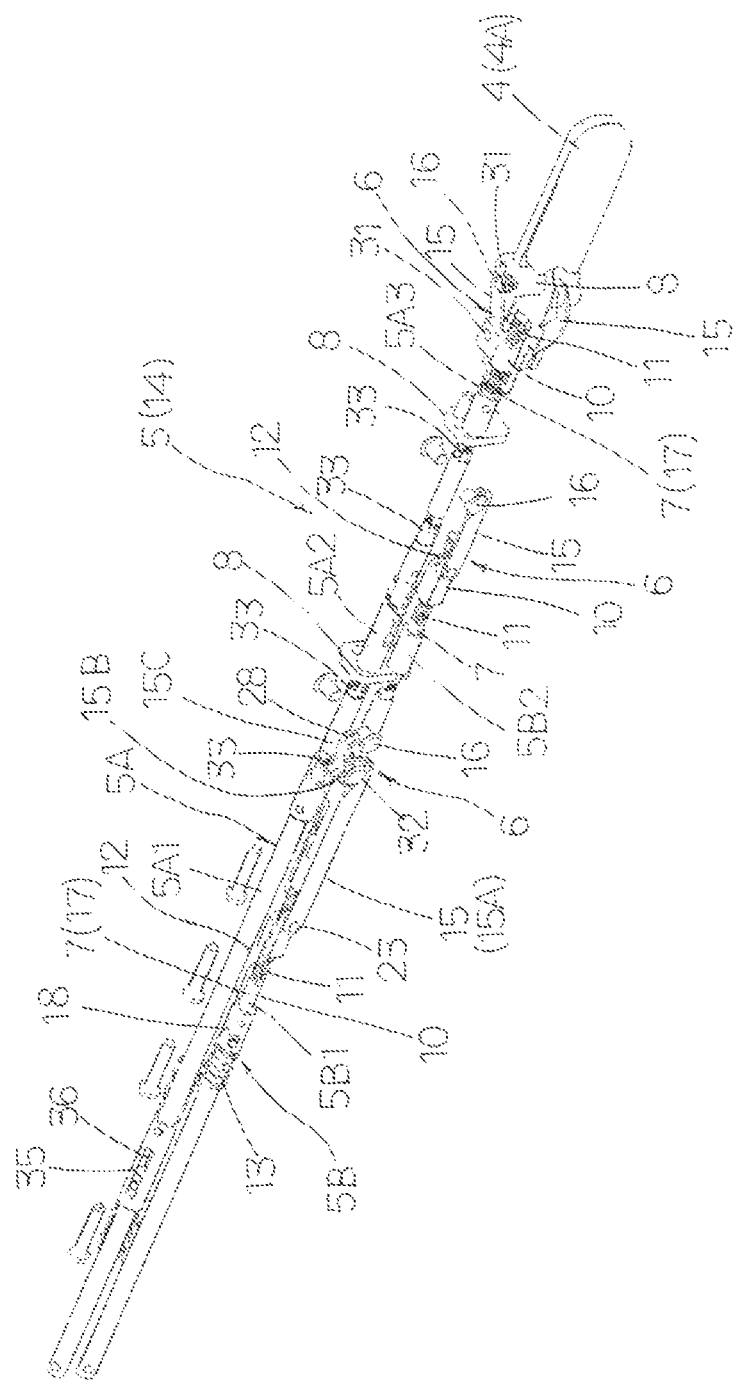
FIG. 2 is a perspective view showing driving means in the forceps of FIG. 1, in which an outer shell is shown removed from forceps of FIG. 1.
Figure 3:
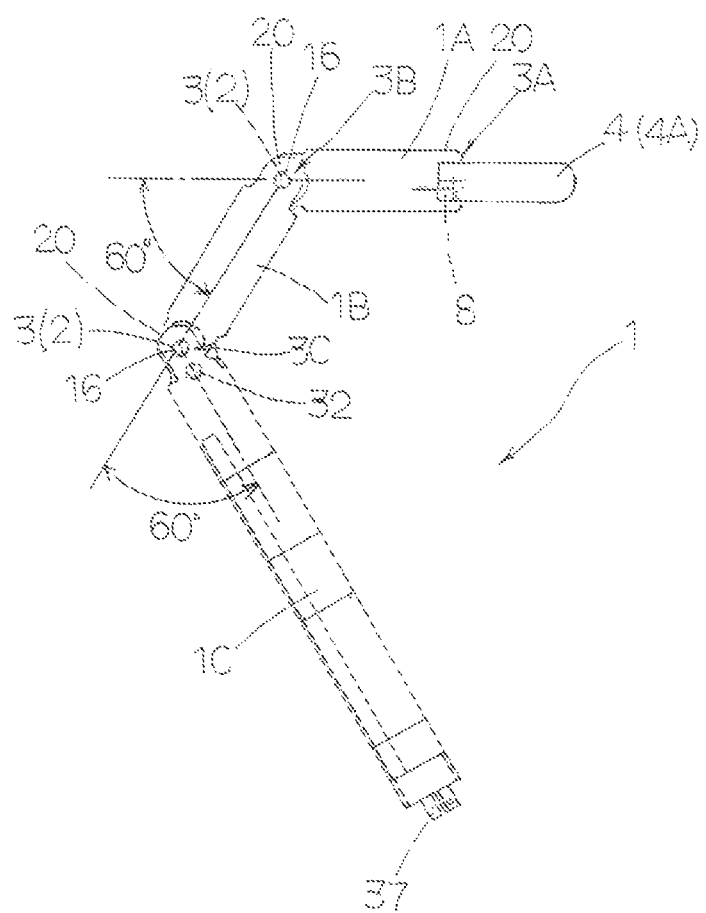
FIG. 3 is a plan view showing the multi-articulated forceps of FIG. 1 in a bent state thereof.
Figure 4:
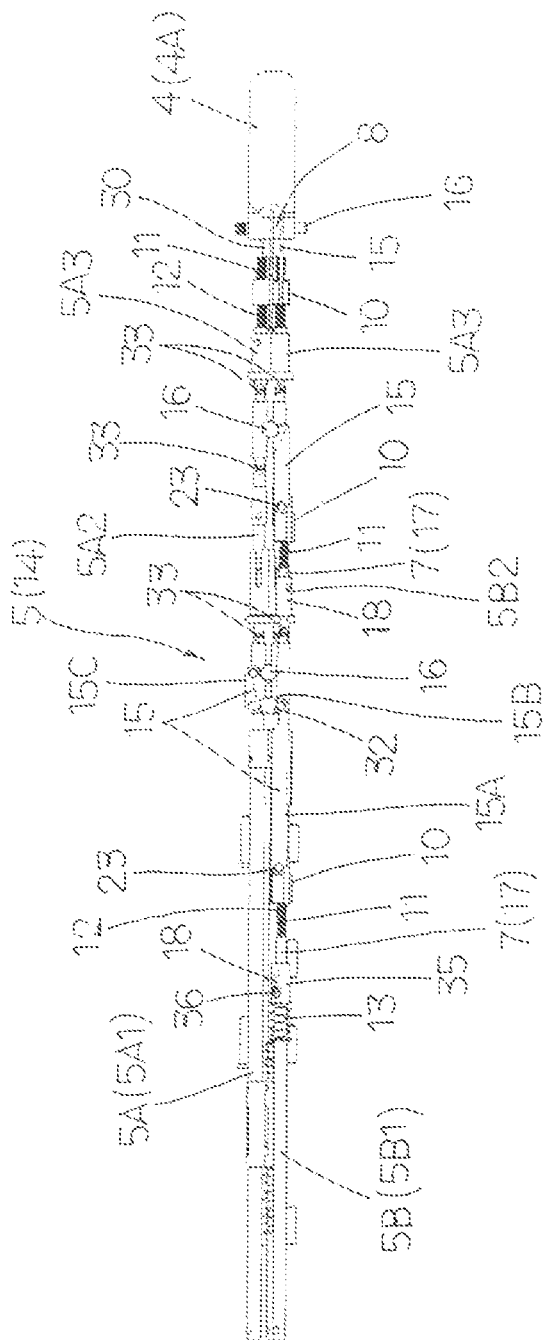
FIG. 4 is a plan view showing the driving means, in which the outer shell is removed from the multi-articulated forceps of FIG. 1.
Figure 5:
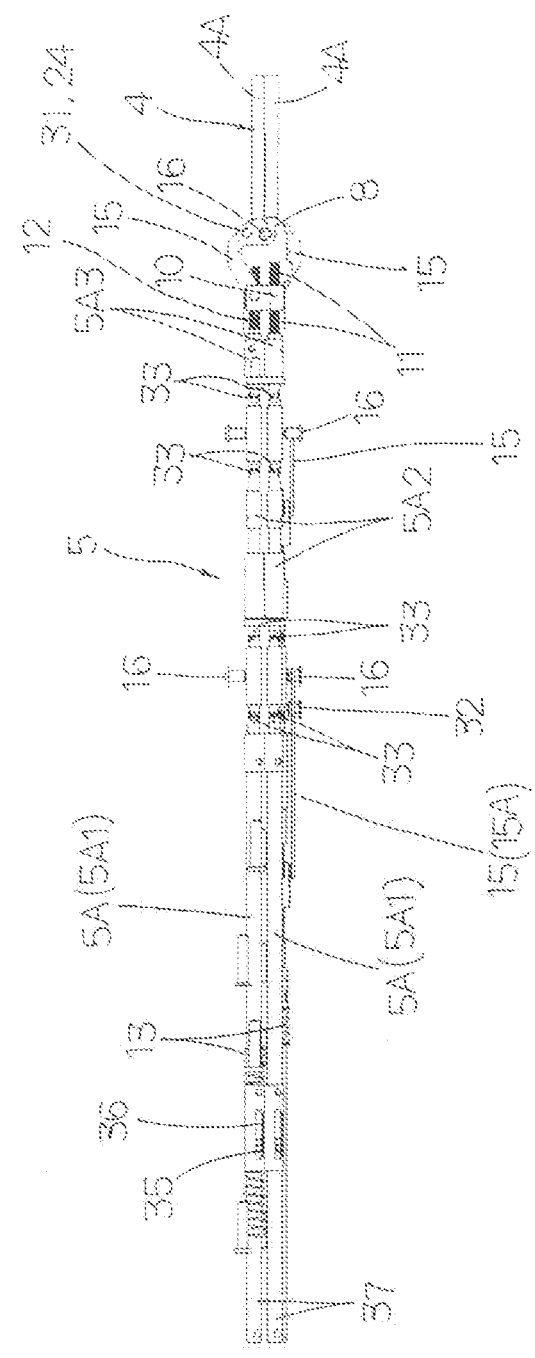
FIG. 5 is a top plan view of the driving means of FIG. 4.
Figure 6:
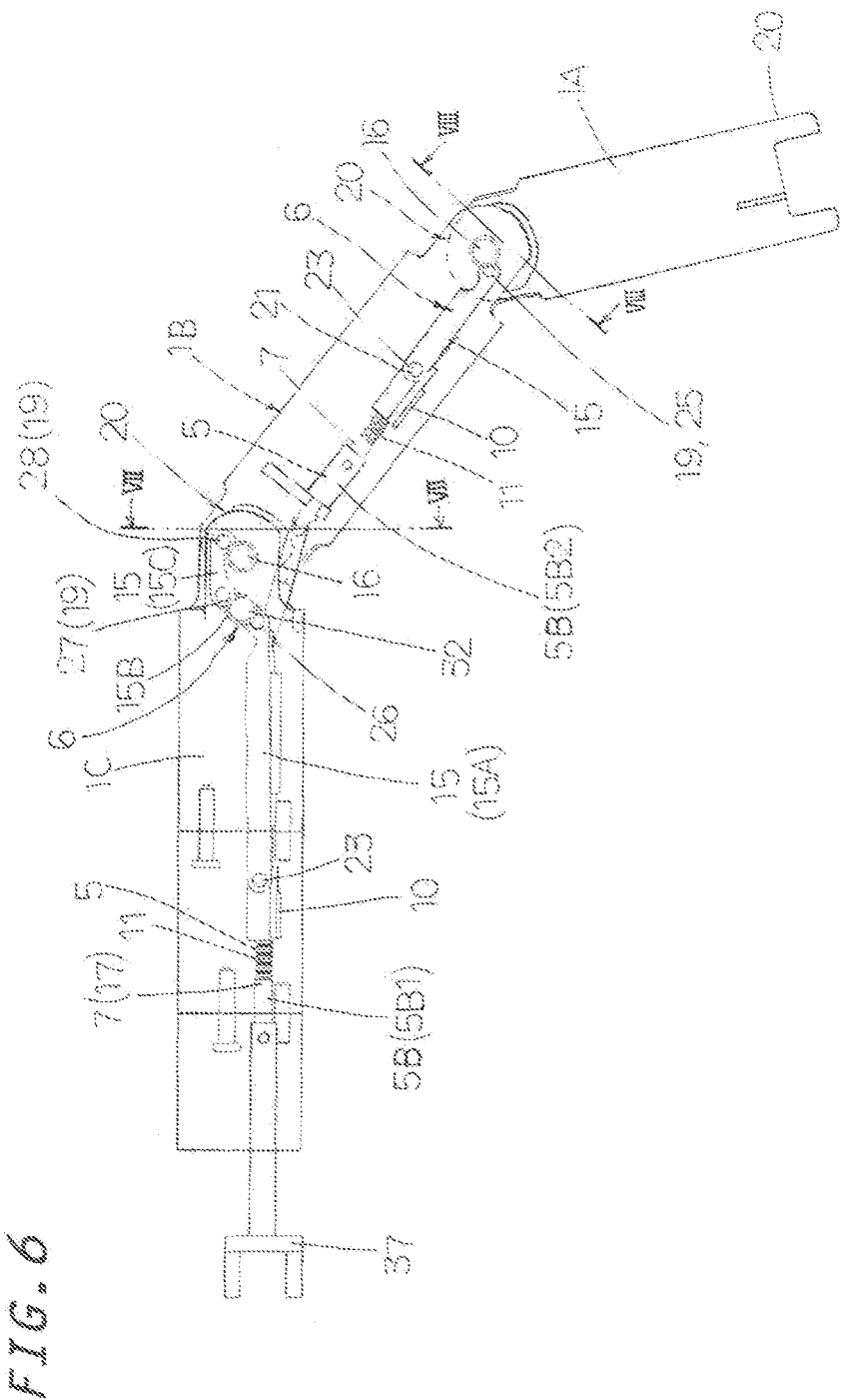
FIG. 6 is a schematic view illustrating of the bending of the outer shell of the multi-articulated forceps of FIG. 1 by means of a linkage mechanism.

The manipulator or forceps having more than one articulation of the present invention is adapted for a variety of instruments applied to for example medical robots, medical instruments, and the like. The manipulator or forceps having more than one articulation of the present invention will be explained in detail with reference to the accompanying drawings. The manipulator or forceps having more than one articulation of the present invention is made smaller than the multi-articulated forceps disclosed in the prior co-pending application. More especially, an outer shell 1 has an outer diameter half of the outer shell in the prior co-pending application, for example, φ8 mm and the power transmission shafts 5 fit into the outer shell 1 are reduced to three in number. Thus, the number of articulations is reduced. Moreover, the multi-articulated forceps get the outer shell 1 to move in a bending manner in the same direction in association with the bending movement between a proximal outer shell 1A and an intermediate outer shell 1B and between the intermediate outer shell 1B and a distal outer shell 1C, so that the proximal outer shell 1 is can rotate in large bending angles. With the multi-articulated forceps constructed as stated earlier, the outer shell 1 and the power transmission shaft 5 are made mainly of metallic material of stainless steel to make sure of a preselected rigidity.

The forceps having more than one articulation of the present invention is mainly composed of more than one hollow outer shell 1 connected each other, more than one articulation 3 to connect in a bending manner adjoining joints 2 lying at opposite ends of the adjacent outer shells 1, a grasping member 4 connected for bending movement to the proximal outer shell 1, a power transmission shaft 5 fit into the outer shells 1 and the articulation 3 for contraction and expansion to allow the grasping member 4 and the outer shells 1 to bend relatively to each other, and an actuator or driving means 14 having a linkage mechanism 6 connecting the power transmission shaft 5 to the outer shell 1. The articulation 3 connects adjacent outer shells 1 to each other in a rocking manner or bending manner at the joints 2 through fulcrum pins 16. The outer shell 1 includes the proximal outer shell 1A having the grasping member 4, the distal outer shell 1C having an operating zone to actuate the power transmission shaft 5, and the intermediate outer shell 1B connecting the proximal outer shell 1A with the distal outer shell 1C. A boss portion 8 is installed inside the outer shell 1. The boss portion 8 provided inside the outer shell 1 has guide holes 34 (refer to FIGS. 7 and 8) in which the power transmission shaft 5 is born and supported and further has a groove (not shown) to guide a linkage member 15, so that the power transmission shaft 5 and the linkage member 15 are constituted so as not to have interference inside the outer shell 1. The driving means 14 is composed of the three power transmission shafts 5, a nut 10 mating with male threads 11 of a threaded portion 12 made around the power transmission shaft 5, and the linkage mechanism 6 connecting the nut 10 to the outer shell 1 in a bending or rotating manner. The driving means 14 is constituted with the power transmission shaft 5 and the linkage member 15. The power transmission shaft 5 has more than one transmission shaft portions 7 which fit into springs 13 to make elongation and shrinkage and further transmission of torque. The linkage member 15 is connected to the transmission shaft portion 7 and arranged to the articulation 3 to make bending movement each other to transmit the torque.

Moreover, the driving means 14 has a claw power transmission shaft 5A and an outer sleeve power transmission shaft 5B. The outer sleeve power transmission shaft 5B is concerned in the bending operation of the proximal outer shell 1A, intermediate outer shell 1B and the distal outer shell 1C. Moreover, the claw power transmission shaft 5A is concerned in the opening/closing movement and the bending movement in the same direction of the claw members 4A. The power transmission shaft 5 is to rotate a pair of claw members 4A independently from each other. The power transmission shaft 5 fits for rotation in the proximal outer shell 1A, the distal outer shell 1C and the intermediate outer shell 1B to move or bend in synchronizing manner in the same direction the proximal outer shell 1A and the intermediate outer shell 1B. Thus, the power transmission shaft 5 is constituted with a single outer shell power transmission shaft 5B which is fastened for rotation to the distal outer shell 1C and the intermediate outer shell 1B. With the multi-articulated forceps of multi-articulated construction, upon rotation of the outer shell power transmission shaft 5B, the nut 10 mating with the male threads 11 moves in axial direction. In response to the movement of the nut 10, the intermediate outer shell 1B bends over, for example, at most 60 degrees with respect to the distal outer shell 1C and at the same time the proximal outer shell 1A bends across at most 60 degrees. The claw power transmission shaft 5A is composed of a distal power transmission shaft 5A1 fit into the distal outer shell 1C, an intermediate power transmission shaft 5A2 fit into the intermediate outer shell 1B, and a proximal power transmission shaft 5A3 arranged in the proximal outer shell 1A. Moreover, the outer shell power transmission shaft 5B is composed of a distal power transmission shaft 5B1 inserted in the distal outer shell 1C, and an intermediate power transmission shaft 5B2 installed in the intermediate outer shell 1B. The claw power transmission shaft 5A is rotated with torque which is transferred through the distal power transmission shaft 5A1 and the intermediate power transmission shaft 5A2, and further the intermediate power transmission shaft 5A2 and the proximal power transmission shaft 5A3 are driven with the torque transferred through universal joints 33 (first universal joint and second universal joint). With the outer shell power transmission shaft 5B, the distal power transmission shaft 5B1 and the intermediate power transmission shaft 5B2 are driven together through the universal joints 33 (third universal joint). The threaded portions 12 of the male threads 11 mating with the nut 10 are formed at the proximal end of the proximal power transmission shaft 5A3 of the claw power transmission shaft 5A and the proximal ends of the distal power transmission shaft 5B1 and the intermediate power transmission shaft 5B2. The linkage mechanism 6 is composed of the nut 10 having the female threads 1 mating with the male threads 11, and more than one linkage member 15 connecting the nut 10 with the outer shell 1. The universal joint 33 is arranged in a zone lying at an intermediate joint 3B and the distal articulation 3C. The claw power transmission shaft 5A and the distal articulation 3C is constituted to make bending at the universal joint 33 in response to the bending movement of the outer shell 1 to transmit the rotating torque.

With the multi-articulated forceps of the present invention, when the claw power transmission shaft 5A and the outer shell power transmission shaft 5B has been rotated, the nut 10 moves in the axial direction along the threaded portions 12 around the male threads 11. The rotating movement of the claw power transmission shaft 5A and the outer shell power transmission shaft 5B causes the axial movement of the nut 10 along the threaded portions 12 of the male threads 11. At the same time, the rotating movement of the claw power transmission shaft 5A and the outer shell power transmission shaft 5B is converted into axial movement along the male threads 11 of the nut 10. Thus, the movement of the nut 10 is converted into a swinging movement of the linkage mechanism 6. The swinging movement of the linkage mechanism 6 causes a swinging movement of the outer shell 1. This swinging movement of the outer shell 1 is converted into the bending or rotating movement of the outer shell 1 or the opening/closing movement of the grasping members 4. It will be thus understood that the linkage mechanism 6 of the linkage members 15 works together with the movement of the nut 10 to make the bending or rotating operation of the opposed outer shells 1. The linkage members 15, though not shown, may be constituted to operate certainly under the guidance of a guiding groove or slit made in the boss portion 8 in the outer shell 1. The nut 10 is mated with male threads 11 formed on the proximal ends of the proximal power transmission shaft 5A3, intermediate power transmission shaft 5B2 and the distal power transmission shaft 5B1, respectively. With the claw members 4A of the grasping members 4 fastened for pivoting movement with respect to the proximal outer shell 1A, moreover, when the distal power transmission shaft 5A1 of the claw power transmission shaft 5A is rotated, the nut 10 moves in the axial direction along the proximal male threads 11 of the proximal power transmission shaft 5A3 and the linkage mechanism 6 of the linkage members 15 moves together whereby the claw members 4A make an opening/closing movement or rotating movement towards the same direction.

The driving means 14 has more than one extendable transmission shaft portion 7 with a spring 13 fit over the shaft portions 7, and the linkage members 15 to provide the linkage mechanism 6 connecting the adjoining transmission shaft portions 7 with each other and lying at joints 3 to make the adjoining transmission shaft portions 7 rotatable and transmitting the torque the linkage members 15. The joints 3 are the areas where the grasping members 4, proximal outer shell 1A and the intermediate 1B are allowed to rotate around the fulcrum pins 16 extending through the boss portions 8 of the grasping members 4, the outer shell 1 and the joints 2. Moreover, the transmission shaft portions 7 is composed of a spring 13, a shaft member 17 on which the spring 13 fits, and a cylinder member 18 which fits over the shaft member 17 to make sliding movement on the shaft member 17 under the resilient force of the spring 13. The transmission shaft portions 7 is kept extended under the action of the resilient force of the spring 13 in the free phase, but contracted after the transmission shaft portions 7 has been assembled in the forceps. The shaft member 17 and the cylinder member 18 are constructed in such a manner that, for example, when a pin 35 installed on the shaft member 17 slides in a slit 36 in the cylinder member 18, the spring 13 exerts a resilient force thereof on the cylinder member 18 to cause abutment of the pin 35 of the shaft member 17 against an end face of the slit 36 to limit the axial sliding area of the cylinder member 18 to the length of the slit 36. With the transmission shaft portions 7 of the power transmission shaft 5, the spring 13 is normally kept in a straight or contracted state. When the joint 3 lying between the ends 20 of the outer shell 1 is rotated, the spring 13 pushes out the cylinder member 18 in a sliding manner to extend the transmission shaft portions 7 at the joints 3 whereby the spring 13 pushes out the cylinder member 18 in a sliding manner to adjust the length at every joint 3.

Moreover, the linkage mechanism 6 includes the linkage members 15 which are connected for rotation to the power transmission shaft 5 and connected for rotation to the outer cylinders 1 with respect to each other at biased pins 19 which are biased in position from the fulcrum pins 16. A pair of claw members 4A of the grasping members 4 is supported in a rocking or rotating manner to the end 20 of the proximal outer shell 1A by the pin 31 to make a swinging movement alternately by the claw power transmission shaft 5A to make opening/closing movement independently from each other and/or bending movement in same direction. Moreover, the joint 3 is composed of a proximal joint 3A to allow a pair of claw members 4A of the grasping members 4 to make opening/closing movement and the bending or rotating movement in the same direction of the claw members 4A, an intermediate joint 3B to rotate the proximal outer shell 1A relatively to the intermediate outer shell 1B, and a distal joint 3C to rotate the intermediate outer shell 1B with respect to the distal outer shell 1C. Moreover, the proximal joint 3A lying between the proximal outer shell 1A and the grasping members 4 is composed of the boss portion 8 of the claw member 4A having a fulcrum pin 16 serving as a center of rotation, and the linkage member 15 fastened to the point 24 of driving action biased from the rotating center and a fulcrum 23 lying at a nut 10 mated with the male threads of the threaded portions 12 of the claw power transmission shaft 5A. Upon rotational movement of the claw power transmission shaft 5A, the nut 10, linkage member 15 and the boss portion 8 are operated together to cause opening/closing movement or rotating movement in the same direction of the claw members 4A.

Figure 8:
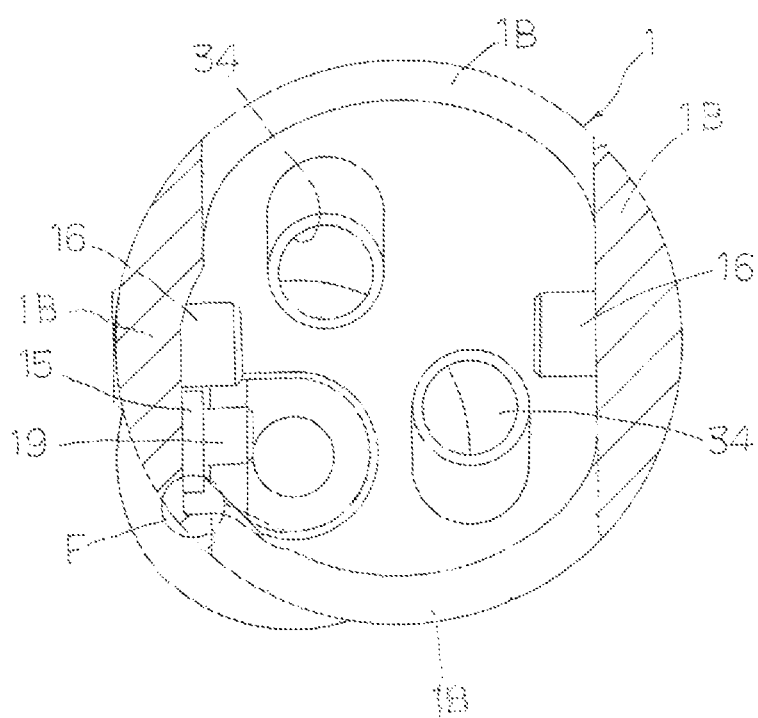
FIG. 8 is a sectional view showing the multi-articulated forceps of FIG. 6, the view being taken on the plane VIII-VIII of FIG. 6 to illustrate an area of an intermediate articulation where the power transmission shaft inserted into a guide hole is removed.

With the multi-articulated forceps of the present invention, an area or space F to allow the operation of the linkage member 15, as shown in FIG. 8, is secured underneath the proximal outer shell 1A. Thus, the linkage member 15 fastened in a swinging manner to the fulcrum 23 of the nut 10 is fastened directly to the point 25 of action on the boss portion 8 of the proximal outer shell 1. The intermediate joint 3B is constituted with the linkage member 15 which is fastened for swinging movement to the fulcrum 23 of the nut 10 mated with the outer shell power transmission shaft 5B lying in the intermediate outer shell 1B and the point 25 of action on the proximal outer shell 1A biased from the rotating center of the fulcrum pin 16 of the proximal outer shell 1A. After the outer shell power transmission shaft 5B has been rotated, the nut 10 lying on the intermediate shell 1B, linkage member 15 and the proximal outer shell 1A serve as the power transmission shaft 5 to rotate the proximal outer shell 1A with respect to the intermediate outer shell 1B. That is, with the linkage mechanism 6 of the intermediate outer shell 1B, the nut 10 mates with the male threads 11 made on the power transmission shaft portions 7 of the intermediate power transmission shaft 5B2 of the outer shell power transmission shaft 5B. The linkage member 15 in the intermediate joint 3B is connected in rocking manner to the pin 21 which is fastened at one end thereof to the nut 10, and connected at another end in rocking manner to the point 24 of driving pin 21 which is provided at the boss portion 8 of the proximal outer shell 1A.

Figure 7:
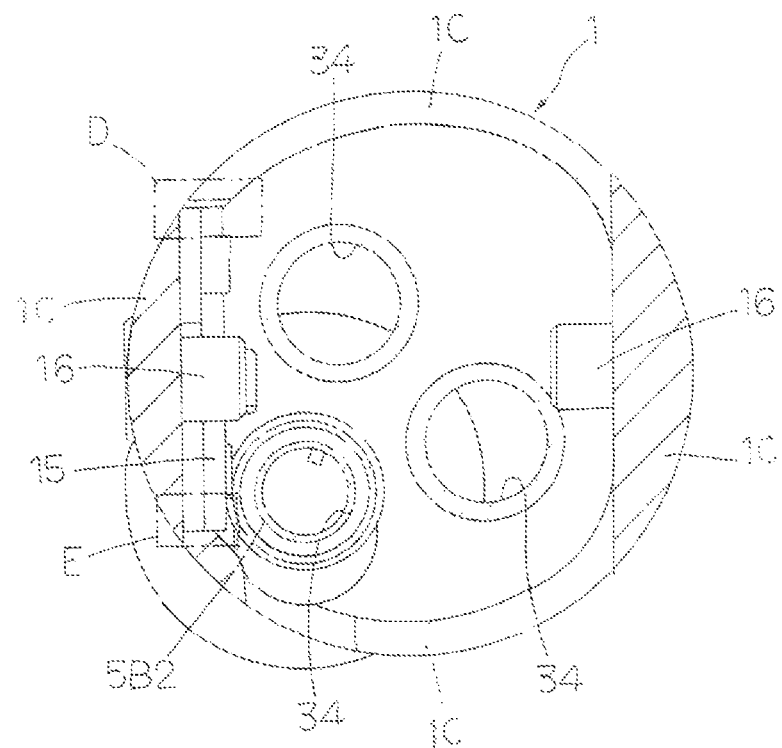
FIG. 7 is a sectional view showing the multi-articulated forceps of FIG. 6, the view being taken on the plane VII-VII of FIG. 6 to illustrate a distal side of the articulation removed from a power transmission shaft to fit into a guide hole.

With the multi-articulated forceps of the present, the distal articulation 3C lying between the intermediate outer shell 1B and the distal outer shell 1C, as shown in FIG. 7 has a spacing at the under area of the intermediate outer shell 1B to accommodate therein the intermediate power transmission shaft 5B2 of the outer shell power transmission shaft 5B so that an area E to get the linkage mechanism 6 to operate has a smaller space. Thus, the linkage mechanism 6 in the distal articulation 3C ensures above the distal outer shell 1C the spacing area D to operate the linkage member 15 to actuate in a rotating manner the outer shell 1 by means of a second linkage member 15B and the third linkage member 15C. With the linkage mechanism 6 in the distal articulation 3C, there is no need to prepare the space below the distal outer shell 1C to operate a first linkage member 15A. With the intermediate joint 3B lying between the distal outer shell 1C and the intermediate outer shell 1B, the linkage mechanism 6 is composed of three linkage members 15, more especially, the first linkage member 15A, second linkage member 15B and the third linkage member 15C. The first linkage member 15A is fastened in rocking manner to a first point 26 of driving action biased from the rotating center of the fulcrum pin 16 of the distal outer shell 1C and a fulcrum 23 on the nut 10 mated with the second linkage member 15B. The second linkage member 15B is fastened in a rocking or pivoting manner around another fulcrum pin 32 to a first point 26 of driving action and the proximal second point 27 of driving action. The third linkage member 15C is connected in a rocking or pivoting manner to the second point 27 of driving action and a third point 28 biased from the rotating center of the fulcrum pin 16 in the intermediate outer shell 1B. With the multi-articulated forceps constructed as stated earlier, upon rotation of the outer shell power transmission shaft 5B, the nut 10, first linkage member 15A, second linkage member 15B and the third linkage member 15C are driven together and the intermediate outer shell 1B and the proximal outer shell 1A in association with each other are rotated relatively to the distal outer shell 1C.

Figure 9:
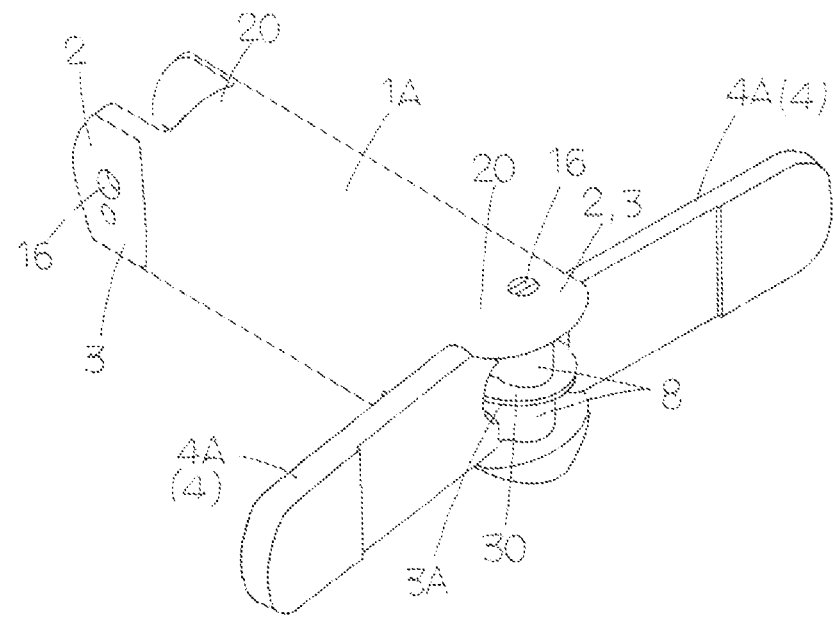
FIG. 9 is a perspective view showing a proximal outer shell and a grasping member in the multi-articulated forceps of the present invention.
Figure 10:
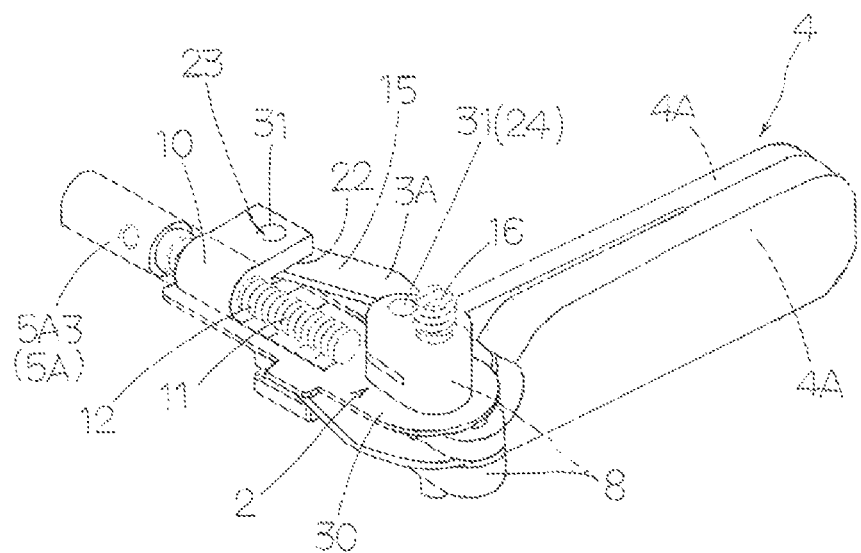
FIG. 10 is a perspective view showing the grasping member and a claw power transmission shaft shown in FIG. 9.

The following describes how claw power transmission shaft 5A actuates the claw members 4A. The claw power transmission shaft 5A as shown in FIGS. 9 and 10 is made in pair and a spacer plate 30 serves to keep a proximal articulation 3A from interference. A nut 10 mates with male threads 11 cut around the proximal member of a power transmission shaft 5A3 of a claw power transmission shaft 5A. A link member 15 is arranged in a slit 22 of the nut 10 for rotation around a pin 31. A pair of the claw members 4A is supported in a rocking or pivoting manner on a boss portion 8 at a fulcrum pin 16. The linkage member 15 is connected for rotation at one end thereof to a pin 31 made on the nut 10 and at another end thereof to another pin 31 which serves as the point of driving action biased from the point of fulcrum of the boss portion 8.

After the distal power transmission shaft 5A1 of one of the claw power transmission shafts 5 is rotated with a manipulator means 37 made on the distal outer shell 1C, the rotation of the distal power transmission shaft 5A1 rotates the intermediate power transmission shaft 5A2 through the universal joint 33 and further rotates the proximal power transmission shaft 5A3 through the universal joint 33. After the proximal power transmission shaft 5A3 has rotated, the male threads 11 made on the proximal end of the proximal power transmission shaft 5A3 rotate to move linearly the nut 10 mated with the male threads 11. Thus, the linear movement of the nut 10 along the male threads 11 moves forward and backward the linkage members 15 which is connected at the fulcrum 23 for rotation or rocking movement to the nut 10. The forward and backward movement of the linkage members 15 causes pulling and/or pushing movement of the claw members 4A to make the opening and closing movements of the claw members 4A. Moreover, another claw power transmission shaft 5A is also actuated as stated earlier. With the multi-articulated forceps constructed as stated earlier, the opening/closing angles between the claw members 4A are 85 degrees on one side of the forceps and about 170 degrees across the claw members 4A.

The following will describe how the outer shell power transmission shaft 5B bends or rotates the intermediate outer shell 1B and the proximal outer shell 1A with respect to the distal outer shell 1C. The outer shell power transmission shaft 5B is composed of the distal power transmission shaft 5B1 and the intermediate power transmission shaft 5B2 to rotate the intermediate outer shell 1B with respect to the distal outer shell 1C through the linkage mechanism 6 in response to the rocking or pivoting movement of the distal power transmission shaft 5B1 in a region of the distal articulation 3C. The proximal outer shell 1A is rotated with respect to the intermediate outer shell 1B through the linkage mechanism 6 in response to the rocking or pivoting movement of the intermediate power transmission shaft 5B2 which makes the rocking or pivoting movement in the same direction in association with the distal power transmission shaft 5B1 in a region of the intermediate articulation 3B. With the multi-articulated forceps constructed as stated earlier, the operational angles of the outer shell 1 is for example as follows. The rocking or pivoting angles of the intermediate outer shell 1B relative to the distal outer shell 1C is about 60 degrees on one side and 120 degrees across the both sides. The rocking or pivoting angles of the proximal outer shell 1A with respect to the intermediate outer shell 1B are about 60 degrees on one side and 120 degrees across the both sides. Thus, since the proximal outer shell 1A and the intermediate outer shell 1B make rocking or pivoting movement or bending or rotating in the same direction in association with each other, the maximum rocking or pivoting angles in total is 240°.

What is claimed is:

1. A multi-articulated manipulator having a driving means which comprises a plurality of hollow outer shells arranged in series in a lengthwise direction, the plurality of hollow outer shells comprising a proximal outer shell, a distal outer shell and at least one intermediate outer shell disposed between the proximal outer shell and the distal outer shell, an articulation connecting adjoining joints of the plurality of outer shells so as to rotate with respect to one another, grasping members connected rotatingly to the proximal outer shell so as to rotate with respect to one another, a power transmission shaft fit into the plurality of outer shells to operate the grasping members to open, close, and rotate, and a linkage mechanism connecting the power transmission shaft with the plurality of outer shells at the articulation to rotate the plurality of outer shells with respect to one another, wherein the grasping members comprise a pair of claw members, and the power transmission shaft is configured to rotate the pair of claw members independently from one another and comprises a pair of claw power transmission shafts fit into the intermediate outer shell and the distal outer shell and mounted for pivoting movement, and an outer shell power transmission shaft fit into the distal outer shell and the intermediate outer shell to be able to rotate the proximal outer shell and the intermediate outer shell in a same direction and further fastened so as to pivot distal outer shell and the intermediate outer shell with respect to one another, wherein the linkage mechanism has nuts having female threads mating with male threads formed on the claw power transmission shaft and the outer shell power transmission shaft, respectively, and a linkage member connecting the nuts with the plurality of outer shells, and wherein upon rotation of the claw power transmission shaft, the nut moves axially along the male threads and the linkage mechanism moves in association with the movement of the nut so as to cause the opening/closing movement or rotating movement in same direction of the claw members, and further upon rotation of the outer shell power transmission shaft, the nut moves axially along the male threads and at the same time the linkage mechanism is operated to rotate the adjacent outer shells relative to each other.

2. The multi-articulated manipulator defined in claim 1, wherein the driving means has a plurality of transmission shafts constructed to extend and shrink under action of springs, a universal joint to connect for rotation of the transmission shafts, and a plurality of linking members to constitute the linkage mechanism to rotatably connect the plurality of linking members to the outer shells.

3. The multi-articulated manipulator defined in claim 2, wherein the transmission shaft extends over the springs, the transmission shaft comprising a shaft portion fit over the springs and a cylinder member fit so as to extend over the shaft portion.

4. The multi-articulated manipulator defined in claim 1, wherein the articulation makes it possible to rotate relative to each other the grasping members, proximal outer shell and the intermediate outer shell around respective fulcrum pins extending through connecting portions between the grasping members and the outer shell to rotatably fasten between the grasping members and the proximal outer shells and between the proximal outer shell and the intermediate outer shell, and between the intermediate outer shell and the distal outer shell.

5. The multi-articulated manipulator defined in claim 4, wherein the linkage member of the linkage mechanism is pivotably connected at one end thereof to the nut and at another end thereof to the outer shell and further connected so as to pivot at a biased location with respect to the fulcrum pin.

6. The multi-articulated manipulator defined in claim 1, wherein the joint is composed of a proximal articulation to make a pair of the claw members of the grasping members close and open relative to each other or rotate in a same direction, an intermediate articulation to rotate the proximal outer shell relative to the intermediate outer shell, and a distal articulation to bend rotate the intermediate outer shell with respect to the distal outer shell.

7. The multi-articulated manipulator defined in claim 1, wherein a pair of claw members for the grasping members is supported in a pivoting manner by the fulcrum pin to a connection fastened to an end of the proximal outer shell to make opening and closing movement or unidirectional rotating movement.

8. The multi-articulated manipulator defined in claim 1, wherein the claw power transmission shaft is composed of a proximal power transmission shaft fit into the proximal outer shell, an intermediate power transmission shaft arranged inside the intermediate outer shell and coupled for rotation to the proximal power transmission shaft through a first universal joint, and a distal power transmission shaft installed in the distal outer shell and coupled for rotation to the intermediate power transmission shaft through a second universal joint and wherein the outer shell power transmission shaft comprises an intermediate power transmission shaft arranged in the intermediate outer shell, and a distal power transmission shaft installed in the distal outer shell and connected for rotation to the intermediate power transmission shaft through a third universal joint.

9. The multi-articulated manipulator defined in claim 6, wherein the proximal articulation lying between the proximal outer shell and the grasping members has the linkage member fastened for a pivoting manner at a driving action point biased from a rotating center of a boss portion of the claw member having the fulcrum pin as the rotating center whereby the nut, linkage member and boss portion work together to open and close or rotate the claw members in the same direction.

10. The multi-articulated manipulator defined in claim 6, wherein the intermediate articulation lying between the proximal outer shell and the intermediate outer shell has the linkage member which is installed for pivoting manner at a fulcrum point in the nut mated with the outer shell power transmission shaft in the intermediate outer shell and at a driving action point in the proximal outer shell biased from a rotating center of the fulcrum pin of the proximal outer shell, and wherein the proximal outer shell the nut, linkage member and the proximal outer shell lying in the intermediate outer shell work together to make the proximal outer shell rotate with respect to the intermediate outer shell, thereby rotating the proximal outer shell relatively to the intermediate outer shell.

11. The multi-articulated manipulator defined in claim 10, wherein the distal articulation between the intermediate outer shell and the distal outer shell is composed of a first linkage member supported in a pivoting manner to a first point of driving action biased from a rotating center of a fulcrum pin point on the distal outer shell and a fulcrum point on the nut mated with the outer shell power transmission shaft lying along the distal outer shell, a second linkage member supported in a pivoting manner around another fulcrum pin to a second point of driving action and a third point of driving action biased from a rotating center of the fulcrum point on the distal outer shell, and a third linkage member fastened for pivoting movement to the second point of driving action and a third point of driving action lying on the intermediate outer shell biased from a rotating center of the fulcrum pin, whereby rotating movement of the outer shell power transmission shaft drives the nut lying on the distal outer shell, the first and second linkage members and the third linkage member, so that the intermediate outer shell and the proximal outer shell are allowed to work together to make the rotating movement.

12. The multi-articulated manipulator defined in claim 1, wherein the outer shell and the power transmission shaft are made of metallic material to have a previously determined rigidity.

* * * * *